United States Patent
Dalmazzone et al.

(10) Patent No.: US 8,038,342 B2
(45) Date of Patent: Oct. 18, 2011

(54) METHOD OF ANALYZING THE KINETICS OF GAS HYDRATE FORMATION IN FLUIDS

(75) Inventors: Christine Dalmazzone, Viroflay (FR); Benjamin Herzhaft, Suresnes (FR); Lionel Rousseau, Issou (FR)

(73) Assignee: Institut Francais du Petrole, Cedex (FR)

( * ) Notice: Subject to any disclaimer, the term of this patent is extended or adjusted under 35 U.S.C. 154(b) by 650 days.

(21) Appl. No.: 11/916,176

(22) PCT Filed: May 24, 2006

(86) PCT No.: PCT/FR2006/001239
§ 371 (c)(1),
(2), (4) Date: Nov. 6, 2008

(87) PCT Pub. No.: WO2006/129018
PCT Pub. Date: Dec. 7, 2006

(65) Prior Publication Data
US 2009/0103586 A1    Apr. 23, 2009

(30) Foreign Application Priority Data
Jun. 2, 2005    (FR) ...................... 05 05685

(51) Int. Cl.
G01K 17/00    (2006.01)
G01N 25/02    (2006.01)

(52) U.S. Cl. ........................................... 374/31; 374/11

(58) Field of Classification Search ................... 436/147; 374/10–12, 16, 27, 28, 31–33, 100, 104, 374/110, 141
See application file for complete search history.

(56) References Cited

U.S. PATENT DOCUMENTS

| | | | |
|---|---|---|---|
| 5,346,306 A * | 9/1994 | Reading et al. | 374/10 |
| 5,660,603 A * | 8/1997 | Elliot et al. | 48/190 |
| 6,571,604 B2 | 6/2003 | Dalmazzone et al. | |
| 6,583,391 B2 * | 6/2003 | Jorimann et al. | 374/11 |
| 2008/0071494 A1 * | 3/2008 | Reading | 374/10 |
| 2009/0034579 A1 * | 2/2009 | Schick | 374/10 |
| 2011/0007775 A1 * | 1/2011 | Wu | 374/11 |
| 2011/0013663 A1 * | 1/2011 | Garden et al. | 374/11 |

FOREIGN PATENT DOCUMENTS
FR    2 859 215    3/2005
* cited by examiner

*Primary Examiner* — Brad Bennett
(74) *Attorney, Agent, or Firm* — Antonelli, Terry, Stout & Kraus, LLP.

(57) ABSTRACT

The present invention relates to a method for determining the kinetics of gas hydrate formation in a fluid comprising water, wherein the following stages are carried out:
  a sample of the fluid is provided in form of a water-in-oil stable emulsion,
  DSC measurements are performed on the sample to obtain at least one peak corresponding to the gas hydrate conversion energy in the water drops of said emulsion,
  kinetic characteristics of the formation of hydrates in said fluid are deduced from the peak.

10 Claims, 3 Drawing Sheets

METHOD OF ANALYZING THE KINETICS OF GAS HYDRATE FORMATION IN FLUIDS

FIELD OF THE INVENTION

The present invention relates to the formation of gas hydrates in fluids comprising water, in particular during hydrocarbon production or drilling operations, notably under deep and very deep offshore conditions. These operating conditions are the cause of particularly complex technical problems linked with the extreme conditions encountered at such great water depths. In fact, temperatures close to 0° C. and pressures close to 400 bars are readily reached at the ocean bottom (mud line), such conditions favouring particularly the formation of gas hydrates in circulating fluids such as effluent, drilling fluids or production fluids. The formation of these gas hydrates, which are solid structures comprising water and gas, can have particularly serious consequences that can even lead to a break in operations and possibly to the destruction of tools and facilities, due to the agglomeration and to the deposition of hydrate crystals in the pipes.

BACKGROUND OF THE INVENTION

In order to solve the problems linked with this hydrate formation risk, operators have to use water-base and/or oil-base well fluids containing additives such as hydrate formation inhibitors. The most commonly used additives are thermodynamic inhibitors whose main purpose is to challenge the temperature and/or pressure limits from which hydrates form. The most commonly used inhibitors are salts and glycols, which poses serious corrosion and toxicity problems while involving high-cost formulations. For oil-base fluids, it is possible to use emulsifying systems efficient in preventing hydrate crystal agglomeration in case of formation (dispersing surfactants or anti-agglomeration agents).

An interesting alternative to thermodynamic inhibition is the use of kinetic inhibitors that do not prevent hydrate formation and whose purpose is to delay the appearance of crystals or to slow down the crystal growth rate.

In order to anticipate hydrate formation risks, one can currently only base oneself on tests carried out with reactors or test loops on more or less simplified fluid formulations, or on model hydrates (THF or freon) allowing to work at atmospheric pressure. The main difficulty for testing formation kinetics in aqueous solutions is linked with the uncertain nature of the nucleation phenomenon that leads to non-reproducible measurements.

In order to overcome this difficulty, hydrates are formed from melting ice or hydrates are made to form by heterogeneous nucleation by adding solid particles to the solutions. At the present time there is no simple, fast and reliable method that is directly applicable, in the laboratory or on site, to real drilling fluids for temperatures close to 0° C. and under natural gas pressure.

The object of the present invention is to provide, in the laboratory or on a drilling site (mud logging cab), or on a production site, a reliable method of determining or analyzing the hydrate formation kinetics on a real well fluid by measuring the heat released upon hydrate crystallization at a given gas pressure, using the DSC (Differential Scanning Calorimetry) method. These measures will allow the operator to compare the kinetics observed with various mud formulations, containing kinetic inhibitors or not, and thus to select the mud formulation that is best suited to the drilling conditions in the case of drilling operations.

This method is in fact applicable to any type of aqueous solution (drilling fluid, cementing fluid, production fluid, production effluent) whose properties as regards gas hydrate formation kinetics have to be known in a reliable and reproducible way.

Gas hydrate formation is a crystallization process that requires a nucleation stage followed by a crystal growth stage. The nucleation process corresponds to the formation of nuclei or "critical germs" in the solution. These critical germs serve as growth sites for the future crystals. Generally, three nucleation types are considered (Mullin J. W., in: Crystallization, London, Butteworths, 1972): —homogeneous primary nucleation, which is spontaneous, —heterogeneous primary nucleation, caused by foreign particles, —and secondary nucleation induced by the crystals already formed.

Nucleation can take place only if the liquid sample breaks through a potential barrier from a thermodynamic point of view. The liquid therefore has to be cooled down below the liquid/solid equilibrium temperature, which means undercooling. Furthermore, formation of the germ being the result of local density fluctuations, the kinetic aspects must be taken into account. It appears that the lower the temperature, the higher the nucleation rate and, consequently, it is extremely difficult to observe crystallization in the neighbourhood of the equilibrium temperature. Another obvious consequence is that there is not one temperature at which crystallization is observed and that this temperature is statistically distributed. It is in fact possible to define only a more probable crystallization temperature, in the statistical sense of the term, which generally depends on the volume of the sample (Clausse D., in: Encyclopedia of Emulsion Technology, Becher P., ed., New York, Marcel Dekker, 1985, vol. 2, p. 77).

In the literature on gas hydrate formation kinetics, most authors emphasize the great experimental difficulty encountered to obtain reproducible results when they study the nucleation of hydrates from an aqueous solution. Many of them decide to overcome this problem by studying nucleation from melting ice. The stage that follows nucleation is crystal growth. The main parameters that govern this stage are the gas diffusion rate, the interfacial area, the pressure, the temperature and, of course, the undercooling degree. Several models have been developed to predict the gas hydrate formation kinetics, but there still is no satisfactory model, mainly because of the nucleation phenomena that are difficult to control experimentally and of the growth models that closely depend on the experimental set-up used (Sloan E. D., "Gas hydrate tutorial", Am. Chem. Soc., Div. Fuel Chem., 42, 2, 449-456).

Considering all these experimental difficulties relative to hydrate formation kinetics, the present invention aims to use the high-pressure DSC (Differential Scanning Calorimetry) technique on stable emulsified systems in order to study the kinetics of gas hydrate formation in drilling fluids.

SUMMARY OF THE INVENTION

The present invention thus relates to a method for determining the kinetics of gas hydrate formation in a fluid comprising water, wherein the following stages are carried out:
  a sample of said fluid is provided in form of a water-in-oil stable emulsion,
  DSC measurements are performed on said sample to obtain at least one peak corresponding to the gas hydrate conversion energy in the water drops of said emulsion,
  kinetic characteristics of the formation of hydrates in said fluid are deduced from the peak.

The fluid can be of aqueous continuous phase type, the emulsion being formed by addition of an organic liquid.

The fluid can also be of oil continuous phase type, in form of a water-in-oil emulsion.

The emulsion stability can be controlled prior to the DSC measurements.

The DSC measurements can be carried out with the gas under pressure.

A hydrate crystallization peak and a hydrate dissociation peak can be determined from the DSC measurements.

A hydrate crystallization peak can be determined by performing at least one isotherm cycle at a predetermined temperature, lower than the dissociation temperature.

According to a variant of the invention: —isotherms can be performed at a lower temperature than the dissociation temperature, said isotherms being of different durations, —hydrates formed after each isotherm of different duration can be heated to obtain a dissociation peak.

A crystallization temperature T1 and a dissociation temperature T1diss can be deduced from said peaks, and at least one kinetic parameter of the formation of hydrates can be deduced from the undercooling degree $\Delta T = T1diss - T1$.

At least one kinetic parameter of the formation of hydrates can be deduced from time t1 when the peak appears and from time t'1 at the vertex of the peak.

BRIEF DESCRIPTION OF THE FIGURES

Other features and advantages of the present invention will be clear from reading the description hereafter, given by way of non limitative example, with reference to the accompanying figures wherein.

DETAILED DESCRIPTION

Figure 1:
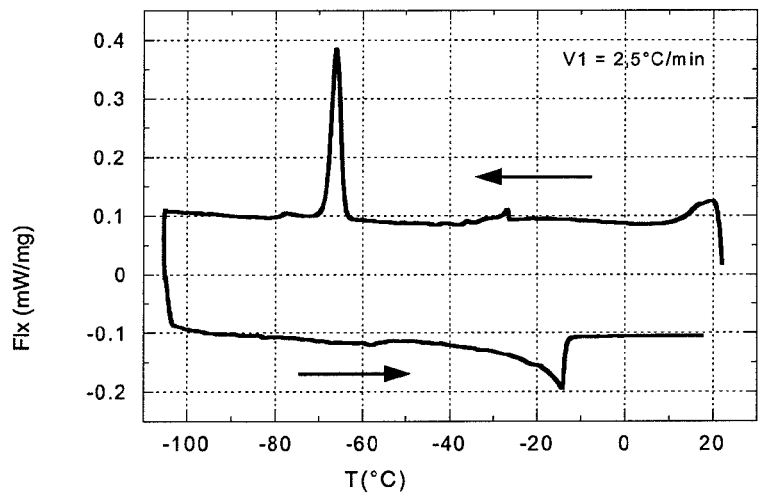
FIG. 1 shows a cooling-heating thermogram for the example of oil-base mud at atmospheric pressure.

HP DSC can be used to determine the gas hydrate dissociation equilibrium points for any type of well fluid, as claimed by document U.S. Pat. No. 6,571,604. From this technique, it is also possible to determine the anti-agglomeration power of a water/oil system towards gas hydrates (patent application FR-04/08,058).

Other advantages of the present invention will be clear from reading the description of the non limitative examples hereafter.

DSC is a technique that allows to measure the heat exchanges between a sample and a reference as a function of time or temperature. These data are collected on a curve referred to as thermogram. There are several types of DSC devices, commercially available. On the other hand, only few can work under controlled pressure. Examples thereof are device DSC111 that can reach a pressure of 100 bars, and device HP micro DSCVII that can reach 400 bars (both marketed by the SETARAM Company—France). A detailed description of the technique and of its thermodynamic applications for hydrates can be found in various publications, notably:

Dalmazzone D, Dalmazzone C, Herzhaft B, SPE Journal 2002, June, 196-202;

Dalmazzone D, Clausse D, Dalmazzone C, Herzhaft B, American Mineralogist 2004, 89, 1183-1191;

Le Parlouër P, Dalmazzone C, Herzhaft B, Rousseau L, Mathonat C, Journal of Thermal Analysis and Calorimetry 2004, 78, 165-172.

According to the present invention that relates to kinetic studies, several types of measurement can be performed after suitable preparation of the sample to be studied.

The gas that is going to form hydrates is selected (methane for example) and an operating pressure P1 is set.

As it has been described, it is fundamental for the sample to come in form of a stable emulsion in order to be able to carry out reliable and reproducible measurements. For oil-base well fluids (in reverse emulsion: water-in-oil), no specific preparation is required, except for homogenization of the sample already in form of an emulsion. Muds referred to as oil-base muds are in fact at the root of emulsions of brine phase in an oil phase. In the case of multiphase oil and water effluents, a first stage consists in preparing a stable emulsion from a sampling.

For water-base muds, we have an aqueous phase which, if it is studied as it is, will give, upon cooling by DSC, different responses, notably as regards the induction time. A large number of samples would have to be studied to obtain a statistical response. In this invention, we emulsify the water-base mud in a non water-miscible liquid that does not crystallize in the temperature range we are dealing with (between −50° C. and 20° C.).

This emulsification can be performed in an oil used for manufacturing oil-base drilling fluids: mineral oil, synthetic oil based on polyalphaolefins or vegetable oil esters such as, for example, HDF 2000 or EDC 99 from Total Solvants, or Radiagreen BDMF (vegetable oil esters) from OLEON.

It is also possible to use any solvent type from petrochemistry: aromatic solvents, aliphatic solvents, isoparaffins, kerosine cuts, gasolines, gas oils, with a preference for non-aromatic solvents and oils for safety reasons.

Crude oils or silicone oils can also be used.

To stabilize the emulsion, any surfactant type of HLB (hydrophile-lipophile balance) ranging between 1 and 10, preferably between 4 and 8, which favours the formation of water-in-oil type emulsions can be used. Non-ionic, anionic or cationic surfactants or surfactant mixtures can be used, preferably non-ionic surfactants or non-ionic, anionic mixtures. The emulsifying system described in document FR-2, 859,215 is preferably used.

The procedure for manufacturing the sample is as follows:
preparing in a vessel the oil continuous phase into which the surfactant system is incorporated,
stirring until dissolution or homogeneous dispersion of the surfactant mixture in the oil phase,
incorporating then the aqueous phase to be studied, dropwise, under gentle stirring, for example with a bar magnet or a low-speed homogenizer. After complete incorporation of the aqueous phase,
carrying out emulsification of the system proper. This emulsification can be performed using any technique known to the person skilled in the art: shaking, shearing with a rotor/stator system of Ultra-Turrax or Polytron type, ultrasounds, shearing in a Couette type system, colloid mill, high-pressure homogenizer, etc. A rotor/stator homogenizer is preferably used.

It is possible to emulsify the aqueous solution using very viscous oils such as silicone oil or paraffin oils. In this case, it is not systematically necessary to add surfactants in order to stabilize the emulsion. The viscosity of the continuous phase can provide sufficient stability.

After emulsification, the sample is ready to be analyzed by DSC. After homogenization of the emulsion under gentle stirring to provide good dispersion of the droplets in the emulsion, 10 and 100 mg emulsion are taken and fed into the measuring cell of the DSC microcalorimeter. The kinetic analysis is then carried out as described below.

First method: The sample in form of an emulsion is first cooled at a constant rate V1 (−1 to −2 K/min) until an exothermic peak corresponding to the crystallization of the hydrates is observed in the thermogram. The temperature corresponding to the vertex of the peak is denoted by T1. The sample is heated at a constant rate until an endothermic peak corresponding to the dissociation of the hydrate is observed. T1 is always lower than equilibrium temperature T1diss corresponding to the hydrate dissociation temperature at pressure P1. The behaviour of another sample can then be compared by carrying out exactly the same experiment, at the same pressure P1 and at the same cooling rate V1. A crystallization temperature T2 is then obtained. The undercooling degree ΔT corresponding to the difference between the equilibrium temperature and the crystallization temperature is then calculated. The greater the undercooling degree observed, the higher the kinetic inhibiting effect. For this method, one has to ensure that only hydrate is formed during continuous cooling, therefore that a single endothermic dissociation peak corresponding to the hydrate considered is obtained, and that no ice melting peak is observed. In fact, if ice forms before or at the same time as the hydrate, this method is not sufficient.

Second method: The sample in form of an emulsion is cooled at a constant rate V1 to an isotherm temperature T'1 ranging between the temperature T1 obtained by continuous cooling as explained in the first method and the equilibrium temperature T1diss corresponding to the hydrate dissociation temperature at pressure P1. If it has not been possible to determine T1 according to the first method, one will experimentally select the isotherm temperatures below T1diss that allow to obtain, upon heating, a single endothermic peak corresponding to the hydrate dissociation, as explained above. Various isotherms are carried out at T'1, with different durations, at P1 (corresponding to the undercooling degree ΔT1=T1diss−T'1). For each isotherm, at the end of the durations selected, the sample is heated at a constant rate (1 to 2 K/min) until the endothermic dissociation peak of the hydrate is obtained. Integration of this dissociation peak allows to draw the curve of the energy released as a function of the isotherm duration. This energy is directly proportional to the amount of hydrates formed. Extrapolation of the curve on the abscissa axis allows to determine a pseudo induction time t'1.

The slope of the curve allows to deduce a crystallization rate. It is then possible to compare the behaviour of another sample by carrying out exactly the same experiment, at the same pressure P1 and at the same isotherm temperature corresponding to the same undercooling degree ΔT1. The line of the curve of energy released as a function of the isotherm duration allows to obtain an induction time t'2 and a crystallization rate. The greater t'2 in relation to t'1, the gentler the slope of the curve, and the greater the kinetic inhibition.

Third method: The sample in form of an emulsion is cooled at a constant rate V1 to an isotherm temperature T'1 ranging between the temperature T1 obtained upon continuous cooling as explained in the first method and the equilibrium temperature T1diss corresponding to the hydrate dissociation temperature at pressure P1. Once T'1 reached (corresponding to an undercooling degree ΔT1), this temperature is kept constant for several hours and the heat exchanges are recorded as a function of time. The formation of hydrates is translated into the appearance of an exothermic peak. The time t'1 referred to as "induction" time, corresponding to the start of the exothermic peak, and the time t1 corresponding to the vertex of the exothermic peak, are recorded. It is also possible to integrate the exothermic crystallization peak as a function of time in order to obtain the energy released per sample mass unit as a function of time. This energy is directly proportional to the amount of hydrates formed. The slope of the curve drawn allows to obtain a crystallization rate. It is then possible to compare the behaviour of another sample by carrying out exactly the same experiment, at the same pressure P1 and at the isotherm temperature corresponding to the same undercooling degree ΔT1. An induction time t'2 and a crystallization time t2 are thus obtained. The greater these times t'2 and t2 in relation to t'1 and t1, the higher the kinetic inhibition. If we draw the released energy curve as a function of time, the gentler the slope, the higher the kinetic inhibition.

In cases where the exothermic hydrate formation peak is not exploitable, the procedure selected is the second indirect method that uses the energy released in dissociation.

EXAMPLE 1

Kinetic Study of an Oil-Base Mud Under a Pressure of 33.5 MPa

Kinetic tests were carried out on an oil-base drilling mud. The composition of the fluid studied is given in the table hereafter. The base oil HDF 2000 is supplied by Total Solvants. The Pliolite DF01 added as filtrate reducer is a product synthesized by the Eliokem Company. The Carbogel clay used is an organophilic clay supplied by BHI. The Radiagreen-Emul emulsifying system is supplied by OLEON NV.

Composition for 1 Liter Oil-Base Mud:

| Compounds | Mass (g) |
| --- | --- |
| HDF 2000 oil | 642.00 |
| Pliolite DF01 resin | 19.26 |
| Radiagreen-Emul (emulsifier) | 13.48 |
| Radiagreen-Emul (co-emulsifier) | 5.78 |
| Lime | 2.60 |
| Carbogel clay | 11.30 |
| Water | 170.00 |
| CaCl2 | 30.00 |
| Weighting material: Barytine (BaSO4) | 385.00 |

The CaCl2 is dissolved in the water phase (15% by weight). This brine is then emulsified in the oil phase containing the other components, using a SILVERSON L4RT agitator at 6000 rpm according to the API's recommendations. If Pliolite DF01 is used as filtrate reducer, the latter is first incorporated to the base oil (15-minute stirring) and left to mature at 80° C. under 170 psi (11.7 b) for 24 hours. Preparation is then continued by adding the other products as recommended by the API.

The mud is thereafter subjected to maturing at 80° C. for 16 hours prior to any handling.

Oil-Base Mud Stability Characterization:

The stability of the emulsion, essential to carry out a reliable kinetic study as explained above, was checked by means of a calorimetric analysis with a DSC at atmospheric pressure. In fact, it is very difficult to measure the size of the water droplets in such a complex emulsion as an oil-base mud, mainly because of the large amount of solids contained in this type of fluid. DSC allows to analyze a mud sample without diluting it, thus without disturbing it. This sample undergoes cooling until crystallization of the water droplets is observed. The lower the crystallization temperature observed, the smaller the drops, and the more stable the emulsion. The applications of this technique to emulsion stability measurement are described in the following document: Dalmazzone, C., Clausse, D., (2001). Microcalorimetry. In Encyclopedic Handbook of Emulsion Technology, (J. Sjöblom, ed.), Marcel Dekker, New York, Chap. 14, pp. 327-347.

In this example, a DSC 2920 TA Instruments is used. A 7.1-mg oil-base mud sample was subjected to a cooling-heating cycle at a sweep rate of 2.5° C./min at atmospheric pressure. Cooling (crystallization of the water drops) was studied between 20° C. and −100° C., and heating (melting of the ice drops) between −100° C. and 20° C. FIG. 1 (heat flow Flx in mW/mg as a function of the temperature T in ° C.) shows the crystallization peak of the water drops of the emulsion observed at very low temperature (−68° C.). The melting peak of the salt water droplets ends at about −15° C., which gives a high undercooling degree ($\Delta T$=melting temperature−crystallization temperature=53° C.). This high undercooling degree, associated with a very narrow and Gaussian crystallization peak, is characteristic of a very fine and stable emulsion. The reproducibility of the cycle shows the stabilized character of the emulsion, which allows the method according to the invention to be implemented.

Kinetic Study of Methane Hydrate Formation in Oil-Base Mud:

For the kinetic study of the formation of methane hydrates in oil-base mud, an HP micro DSCVII device marketed by SETARAM was used to allow to work under controlled methane pressure up to 40 MPa. A first sweep at $V1=1°$ C./min under 33.5 MPa methane allowed to determine the dissociation temperature T1diss (about 14° C.) and the crystallization temperature T1 (about −25° C.) (first method). We then studied the formation of hydrates for various isotherms T'1 ranging between T1 and T1diss, because the formation peak is entirely detectable at this pressure (third method).

Figure 2:
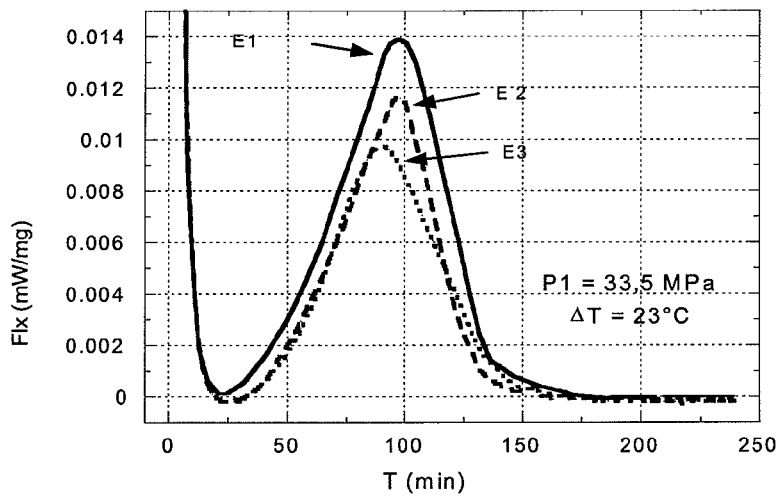
FIG. 2 shows thermograms of the formation of methane hydrate in oil-base mud for an isotherm at T'1=−9° C. ($\Delta T1=23°$ C., P1=33.5 MPa), reproducibility on 3 tests.

FIG. 2 shows the thermograms obtained during reproducibility tests E1, E2, E3 carried out at an isotherm temperature T'1 of −9° C. ($\Delta T1=23°$ C., P1=33.5 MPa, V1=1° C./min).

The good reproducibility of induction times t'1 of the order of 25 min (start of the exothermic peak) and of times t1 corresponding to the vertex of the exothermic peaks ranging between 80 and 100 min can be observed.

Figure 3:
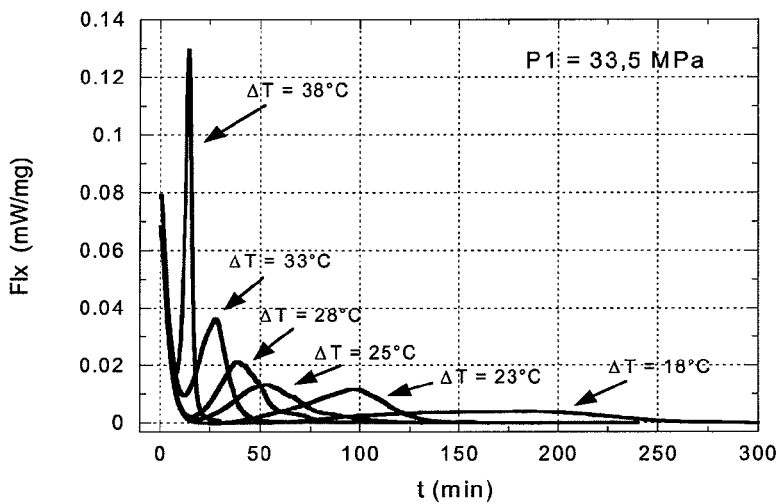
FIG. 3 shows the thermograms obtained upon the formation of methane hydrates with isotherms at T'1=−4, −9, −11, −14, −19 and −24° C. (i.e. $\Delta T1=18, 23, 25, 28, 33$ and $38°$ C. respectively) at P1=33.5 MPa.

FIG. 3 shows the thermograms obtained upon the formation of methane hydrates with isotherms at T'1=−4, −9, −11, −14, −19 and −24° C. (i.e. $\Delta T1$=18, 23, 25, 28, 33 and 38° C. respectively) at P1=33.5 MPa.

The increase of induction times t'1 and of times t1 corresponding to the vertex of the exothermic peaks with the decrease of the undercooling degree $\Delta T1$ can be noted. These kinetics were reproduced for P1=13.5 MPa and 23.5 MPa and the same behaviours were observed.

Figure 4:
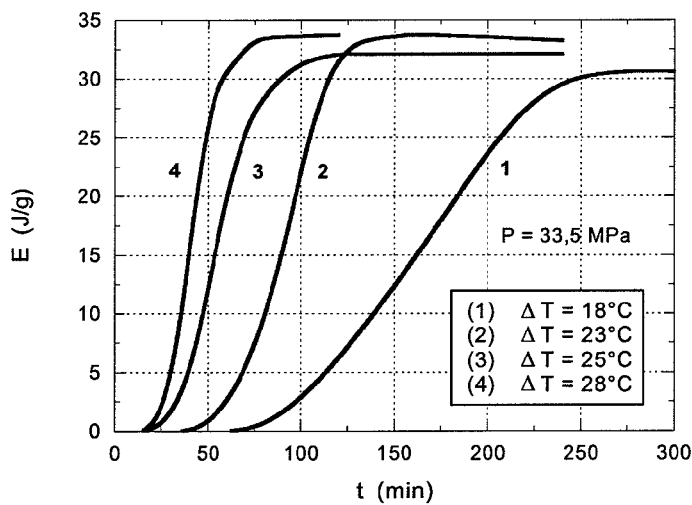
FIG. 4 shows the curves of energy E released per sample mass unit as a function of time, for $\Delta T1=18, 23, 25$ and $28°$ C., FIG. 5 gives the percentage of hydrates (% Hy) formed as a function of time for isotherms at −10, −15 and −21° C. ($\Delta T1=16, 21$ and $26°$ C. respectively) at P1=11 MPa.

It is also possible to integrate the exothermic crystallization peak as a function of time in order to obtain the energy E (J/g) released per sample mass unit as a function of time (FIG. 4). This energy E is directly proportional to the amount of hydrates formed. The slope of the curve obtained is related to a crystallization rate.

Figure 5:
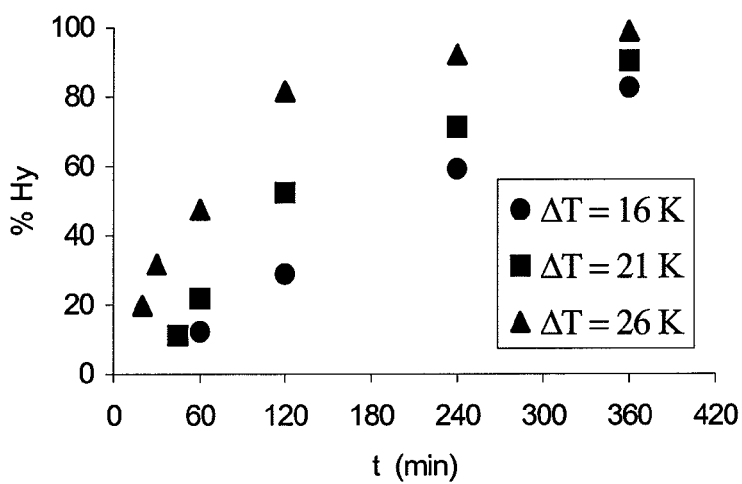

Finally, it can be noted that, for the lower pressures (<12 MPa), it can be very difficult to observe the exothermic hydrate formation peak during the isotherms. In this case, the second method described above is used. The hydrate formation kinetics was studied according to this method with a DSC111 SETARAM calorimeter. The test pressure was P1=11 MPa. The sample was cooled at a constant rate $V1=1°$ C./min down to an isotherm temperature T'1 ranging between temperature T1 obtained upon continuous cooling as in the first method and the equilibrium temperature T1diss corresponding to the hydrate dissociation temperature at pressure P1. After various isotherm durations at P1 and at undercooling degree $\Delta T1$ (T1diss−T'1), the sample was heated at a constant rate (1° C./min) until an endothermic hydrate dissociation peak was obtained. Integration of this dissociation peak allows to draw the curve of energy release as a function of the isotherm duration. This energy is directly proportional to the amount of hydrates formed. The results are given in FIG. 5. Extrapolation of the curve on the abscissa axis allows to determine a pseudo induction time t1. The slope of the curve is related to a crystallization rate.

EXAMPLE 2

Kinetic Study of a Solid-Free Water-Base Mud Under a Pressure of 23.5 MPa

The same type of kinetic study was carried out on a solid-free water-base mud referred to as BSS. This mud, having the following composition, was prepared according to the API's recommendations with a Hamilton Beach agitator (10,000 rpm).

Composition for 1 Liter Solid-Free Water-Base Mud (BSS):

| Compounds | Mass (g) | Mixing order | Hamilton Beach |
|---|---|---|---|
| Water | 350.00 | 1 | |
| Xanthan | 1.40 | 2 | 5 min |
| Starch | 4.20 | 3 | 5 min |
| Non-ionic polyacrylamide | 1.75 | 4 | 5 min |
| Monoethylene glycol | 17.50 | 5 | 5 min |
| NaCl | 70.00 | 6 | 5 min |
| Bactericide (NaN3) | 0.14 | 7 | 5 min |
| | | | +10 min |
| | | | +16 h static |

This mud was studied as it was to achieve a kinetic study. None of the aforementioned methods (1, 2 or 3) allowed to obtain reproducible results.

According to the present invention, a stable emulsion of water/oil type was prepared from this mud so as to be able to statistically study the formation of methane hydrates. The composition and the preparation mode are summed up in the table hereafter. The continuous phase of the emulsion was first prepared from an HDF2000 base oil (Total Solvants) to which the emulsifying mixture used for the oil-base mud described in example 1 was added (Radiagreen Emul: emulsifier and co-emulsifier by OLEON NV). The mixture was stirred with an Ultra-Turrax homogenizer at 6000 rpm for 1 min, then the water-base mud BSS was added dropwise. When the entire aqueous phase was incorporated, the speed was increased to 9500 rpm and stirring continued for 5 minutes.

Composition and Preparation of the Emulsion Tested:

| Compounds | Mass (g) |
|---|---|
| HDF 2000 | 40.00 |
| Radiagreen Emul (emulsifier) | 1.60 |
| Radiagreen Emul (co-emulsifier) | 0.48 |
| 1 minute at 6000 rpm (Ultra-Turrax) | |
| BSS | 10 (dropwise at 6000 rpm) |
| 5 minutes at 9500 rpm (Ultra-Turrax) | |

Figure 6:
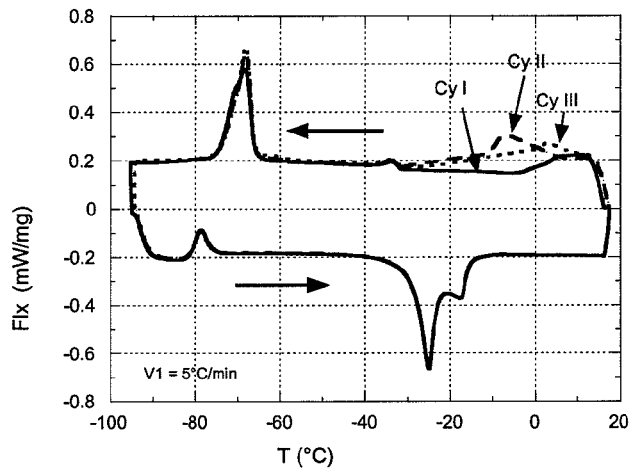
FIG. 6 shows the cooling-heating thermograms of the water-in-oil base mud emulsion, at atmospheric pressure.

Tested Emulsion Stability Characterization:

The stability of the water-in-oil type emulsion was tested by calorimetry with a DSC 2920 TA Instruments at atmospheric pressure. A 5.7-mg sample was subjected to 3 cooling-heating cycles (Cy I, Cy II, Cy III) with a sweep rate of 5° C./min between 20° C. and −90° C. FIG. 6 shows that the emulsion is perfectly stable since a narrow and relatively Gaussian peak is obtained for the crystallization of the water drops in the mud at a very low temperature (about −68° C.), which does not vary even after several thermal cycles.

Figure 7:
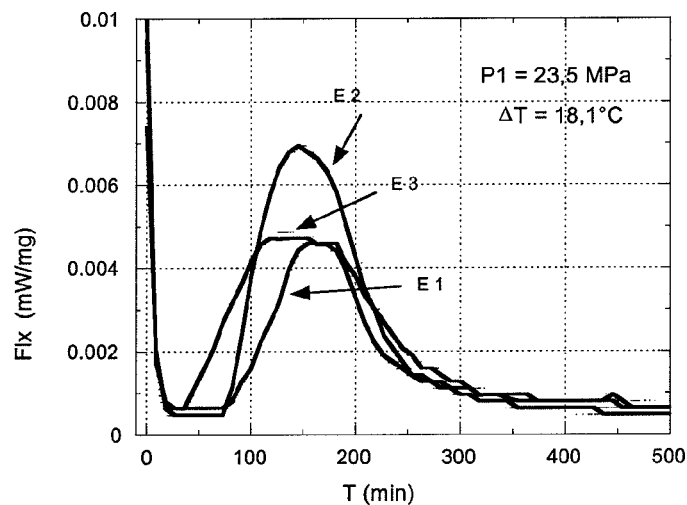
FIG. 7 shows thermograms of the formation of methane hydrate in the water-base mud emulsion for an isotherm at T'1=−10° C. ($\Delta T1=18°$ C., P1=23.5 MPa), reproducibility on 3 tests E1, E2, E3.

For the kinetic study of methane hydrate formation in the water-base mud emulsion, we used an HP micro DSCVII from SETARAM at a methane pressure P1 of 23.5 MPa. A first sweep at V1=1° C./min at this methane pressure allowed to determine the dissociation temperature T1diss (about 8° C.). On the other hand, in the case of this mud, it was not possible to determine T1 because ice formed at the same time as hydrates upon continuous cooling. We studied the formation of hydrates at different isotherms T'1 below T1diss because the formation peak is totally detectable at this pressure (method 3), and we selected the isotherm temperatures for which a single endothermic peak corresponding to the dissociation of the methane hydrate upon heating was observed. The reproducibility of the measurements was checked on 3 different emulsions (see FIG. 7 for $\Delta T1$=18° C., P1=23.5 MPa, V1=1° C./min).

Figure 8:
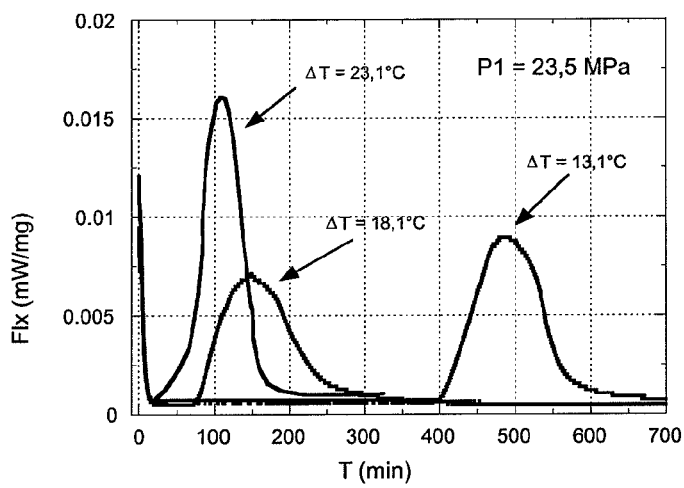
FIG. 8 shows the thermograms obtained upon methane hydrate formation with isotherms at T'1=−5, −10 and −15° C. (i.e. $\Delta T1=13, 18$ and $23°$ C. respectively) at P1=23.5 MPa.

FIG. 8 shows the thermograms obtained upon methane hydrate formation with isotherms at T'1=−5, −10 and −15° C. (i.e. $\Delta T1$=13, 18 and 23° C. respectively) at P1=23.5 MPa.

The increase of induction times t'1 and of times t1 corresponding to the vertex of the exothermic peaks with the decrease of the undercooling degree $\Delta T1$ can be noted.

EXAMPLE 3

Effects of a Kinetic Inhibitor at 23.5 MPa

In this example, we studied the effect of a product used as a kinetic hydrate formation inhibitor for applications in petroleum production. It is the Hytreat product supplied by TR Oil Services (TROS, Aberdeen). It was tested in a proportion of 0.5% by weight incorporated in the water-base mud studied in example 2. After incorporation of the kinetic inhibitor, the water-base mud was emulsified according to the same procedure as above in a continuous oil phase, as shown in the table hereafter.

Composition and Preparation of the Emulsion Tested:

| Compounds | Mass (g) |
|---|---|
| HDF 2000 | 40.00 |
| Radiagreen Emul (emulsifier) | 1.60 |
| Radiagreen Emul (co-emulsifier) | 0.48 |
| 1 minute at 6000 rpm (Ultra-Turrax) | |
| BSS + 0.5 wt % inhibitor | 10 |
| (10 minutes magnetic agitator) | (dropwise at 6000 rpm) |
| 5 minutes at 9500 rpm (Ultra-Turrax) | |

Kinetic test for $\Delta T1$ = 18° C., P1 = 23.5 MPa and V1 = 1° C./min

Figure 9:
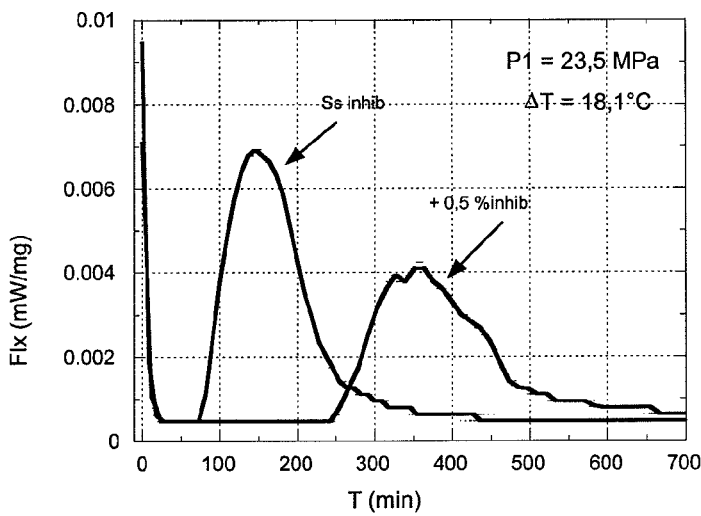
FIG. 9 shows the thermograms obtained upon methane hydrate formation with isotherms at T'1=−10° C. (i.e. $\Delta T1=18°$ C.) at P1=23.5 MPa, with or without kinetic inhibitor in the emulsified water-base mud.

FIG. 9 shows the hydrate formation peaks obtained with an isotherm at −10° C. (P1=23.5 MPa and V1=1° C./min). It can be observed that the kinetic inhibitor tested under these conditions (curve 0.5% inhib) allows to increase induction time t'1 from 70 minutes (curve Ss inhib) to about 250 minutes, and the time t1 corresponding to the vertex of the peak from 150 to 350 minutes.

The present invention is not limited to drilling or completion fluids, its scope extends to any fluid likely to form gas hydrates and for which knowledge of the formation kinetics is important.

The invention claimed is:

1. A method for determining the kinetics of gas hydrate formation in a fluid comprising water, wherein the following stages are carried out:
    a sample of said fluid is provided in form of a water-in-oil stable emulsion,
    DSC measurements are performed on said sample to obtain at least one peak corresponding to the gas hydrate conversion energy in the water drops of said emulsion,
    kinetic characteristics of the formation of hydrates in said fluid are deduced from the peak.

2. A method as claimed in claim 1, wherein said fluid is of aqueous continuous phase type, said emulsion being formed with addition of an organic liquid.

3. A method as claimed in claim 1, wherein said fluid is of oil continuous phase type in water-in-oil emulsion.

4. A method as claimed in claim 1, wherein the stability of said emulsion is controlled prior to DSC measurements.

5. A method as claimed in claim 1, wherein the DSC measurements are performed with said gas under pressure.

6. A method as claimed in claim 1, wherein a hydrate crystallization peak and a hydrate dissociation peak are determined.

7. A method as claimed in claim 1, wherein a hydrate crystallization peak is determined by carrying out at least one isotherm cycle at a predetermined temperature lower than the dissociation temperature.

8. A method as claimed in claim 1, wherein:
    isotherms are performed at a lower temperature than the dissociation temperature, said isotherms being of different durations,
    hydrates formed after each isotherm of different duration are heated to obtain a dissociation peak.

9. A method as claimed in claim 6, wherein a crystallization temperature T1 and a dissociation temperature T1diss are deduced from said peaks, and at least one kinetic parameter of the formation of hydrates is deduced from the undercooling degree $\Delta T=T1diss-T1$.

10. A method as claimed in claim 7, wherein at least one kinetic parameter of the formation of hydrates can be deduced from time t1 when the peak appears and from time t'1 at the vertex of the peak.

* * * * *